US010750930B2

(12) United States Patent
Takahashi et al.

(10) Patent No.: US 10,750,930 B2
(45) Date of Patent: Aug. 25, 2020

(54) ENDOSCOPE APPARATUS AND METHOD FOR OPERATING ENDOSCOPE APPARATUS

(71) Applicant: SONY CORPORATION, Tokyo (JP)

(72) Inventors: Yasuaki Takahashi, Kanagawa (JP);
Koji Kashima, Kanagawa (JP);
Hisakazu Shiraki, Kanagawa (JP);
Toru Mitome, Tokyo (JP)

(73) Assignee: SONY CORPORATION, Tokyo (JP)

( * ) Notice: Subject to any disclaimer, the term of this patent is extended or adjusted under 35 U.S.C. 154(b) by 483 days.

(21) Appl. No.: 15/521,430

(22) PCT Filed: Oct. 23, 2015

(86) PCT No.: PCT/JP2015/079922
§ 371 (c)(1),
(2) Date: Apr. 24, 2017

(87) PCT Pub. No.: WO2016/072288
PCT Pub. Date: May 12, 2016

(65) Prior Publication Data
US 2017/0303770 A1 Oct. 26, 2017

(30) Foreign Application Priority Data
Nov. 6, 2014 (JP) .................. 2014-226054

(51) Int. Cl.
A61B 1/00 (2006.01)
A61B 1/313 (2006.01)
(Continued)

(52) U.S. Cl.
CPC ........ *A61B 1/00048* (2013.01); *A61B 1/0005* (2013.01); *A61B 1/0051* (2013.01);
(Continued)

(58) Field of Classification Search
CPC combination set(s) only.
See application file for complete search history.

(56) References Cited

U.S. PATENT DOCUMENTS 4,895,431 A * 1/1990 Tsujiuchi ............... A61B 1/042
359/29
5,982,953 A * 11/1999 Yanagita ............... G06F 19/321
348/580
(Continued)

FOREIGN PATENT DOCUMENTS

CN 101778592 A 7/2010
CN 102802498 A 11/2012
(Continued)

OTHER PUBLICATIONS

Extended European Search Report of EP Patent Application No. 15857144.8, dated Jan. 22, 2018, 8 pages.
(Continued)

Primary Examiner — John P Leubecker
Assistant Examiner — Shankar Raj Ghimire
(74) Attorney, Agent, or Firm — Chip Law Group

(57) ABSTRACT

The present technology relates to an endoscope apparatus configured to be capable of assisting with setting of an angle of view of immediately before an endoscope is pulled out when the endoscope is pulled out and cleaned and then reinserted during surgery in endoscopic surgery and the like, and a method and program for operating the endoscope apparatus. An image captured by the endoscope apparatus is recorded, a feature value of the image captured is detected, a difference between detected feature values of consecutive images is obtained, and, when the difference is greater than a predetermined threshold value, an index is added to the image captured. Thus, the index is added to an image of immediately before the endoscope is pulled out from a body cavity, and the image is recorded. Then, when the endoscope
(Continued)

is pulled out and then reinserted, the images each to which the index is added are displayed as a list, and information indicating an angle of view in an image selected is displayed to be superimposed on information indicating an angle of view of an image currently captured after reinsertion, whereby assist display to an original angle of view is obtained. The present technology can be applied to the endoscope apparatus.

15 Claims, 9 Drawing Sheets

(51) Int. Cl.
*A61B 1/005* (2006.01)
*G02B 23/24* (2006.01)

(52) U.S. Cl.
CPC .......... *A61B 1/00193* (2013.01); *A61B 1/313* (2013.01); *A61B 1/00009* (2013.01); *A61B 1/00039* (2013.01); *G02B 23/2484* (2013.01)

(56) References Cited

U.S. PATENT DOCUMENTS

| | | | | |
|---|---|---|---|---|
| 7,951,070 | B2* | 5/2011 | Ozaki | A61B 1/00009 600/104 |
| 2002/0183590 | A1* | 12/2002 | Ogawa | A61B 1/00041 600/117 |
| 2005/0033117 | A1 | 2/2005 | Ozaki et al. | |
| 2005/0215854 | A1* | 9/2005 | Ozaki | A61B 1/00009 600/109 |
| 2006/0058624 | A1* | 3/2006 | Kimura | A61B 5/055 600/407 |
| 2007/0173689 | A1 | 7/2007 | Ozaki et al. | |
| 2008/0214907 | A1* | 9/2008 | Gutkowicz-Krusin | A61B 5/0059 600/306 |
| 2009/0177034 | A1* | 7/2009 | Urakawa | A61B 1/041 600/109 |
| 2009/0227864 | A1* | 9/2009 | Sato | A61B 1/0005 600/424 |
| 2010/0198008 | A1 | 8/2010 | Kawano | |
| 2012/0062717 | A1* | 3/2012 | Kinouchi | A61B 1/00009 348/74 |
| 2013/0002844 | A1* | 1/2013 | Shida | A61B 1/00009 348/65 |
| 2013/0197357 | A1* | 8/2013 | Green | A61B 8/0841 600/424 |
| 2014/0204187 | A1* | 7/2014 | Sasaki | A61B 1/00009 348/65 |
| 2014/0258918 | A1* | 9/2014 | Morishima | A61B 6/463 715/783 |
| 2015/0018618 | A1* | 1/2015 | Ikeda | G02B 23/2415 600/111 |
| 2015/0073265 | A1 | 3/2015 | Popovic et al. | |
| 2015/0223670 | A1* | 8/2015 | Fujita | A61B 1/00036 600/109 |
| 2016/0259159 | A1* | 9/2016 | Matsui | G02B 23/26 |
| 2016/0262624 | A1* | 9/2016 | Nakajima | A61B 5/444 |
| 2017/0014017 | A1* | 1/2017 | Obara | A61B 1/00009 |

FOREIGN PATENT DOCUMENTS

| | | |
|---|---|---|
| CN | 104185441 A | 12/2014 |
| CN | 104244800 A | 12/2014 |
| CN | 104755007 A | 7/2015 |
| EP | 2189102 A1 | 5/2010 |
| EP | 2425761 A1 | 3/2012 |
| EP | 2550909 A1 | 1/2013 |
| EP | 2838412 A1 | 2/2015 |
| EP | 2856927 A1 | 4/2015 |
| EP | 2912987 A1 | 9/2015 |
| JP | 2012-170774 A | 9/2012 |
| JP | 2013-244362 A | 12/2013 |
| JP | 5427036 B2 | 2/2014 |
| JP | 2014-83289 A | 5/2014 |
| JP | 2015-514492 A | 5/2015 |
| WO | 2009/022667 A1 | 2/2009 |
| WO | 2011/118287 A1 | 9/2011 |
| WO | 2011/142189 A1 | 11/2011 |
| WO | 2013/156893 A1 | 10/2013 |
| WO | 2013/179855 A1 | 12/2013 |

OTHER PUBLICATIONS

International Search Report and Written Opinion of PCT Application No. PCT/JP2015/079922, dated Jan. 19, 2016, 06 pages of English Translation and 06 pages of ISRWO.

International Preliminary Report on Patentability of PCT Application No. PCT/JP2015/079922, dated May 18, 2017, 07 pages of English Translation and 03 pages of IPRP.

Office Action for JP Patent Application No. 2016-557704, dated Jul. 4, 2019, 07 pages of Office Actin and 07 pages of English Translation.

* cited by examiner

ENDOSCOPE APPARATUS AND METHOD FOR OPERATING ENDOSCOPE APPARATUS

CROSS REFERENCE TO RELATED APPLICATIONS

This application is a U.S. National Phase of International Patent Application No. PCT/JP2015/079922 filed on Oct. 23, 2015, which claims priority benefit of Japanese Patent Application No. JP 2014-226054 filed in the Japan Patent Office on Nov. 6, 2014. Each of the above-referenced applications is hereby incorporated herein by reference in its entirety.

TECHNICAL FIELD

The present technology relates to an endoscope apparatus, and a method and program for operating the endoscope apparatus, and in particular relates to an endoscope apparatus configured to be capable of assisting in obtaining an image capture state of immediately before a scope of the endoscope apparatus is pulled out when the scope is pulled out and reinserted, and a method and program for operating the endoscope apparatus.

BACKGROUND ART

Laparoscopic surgery using an endoscope apparatus is becoming common.

The laparoscopic surgery is an operative procedure for performing surgery by making several holes in skin around an affected part of a human body, setting a fixed hole called a trocar, inserting a rod-shaped endoscope scope connected to an endoscope apparatus from one of the holes to capture an image, and inserting a rod-shaped forceps from other holes to perform the surgery on the affected part while checking the affected part by displaying the image on a display and the like.

For this reason, it is generally said that in the laparoscopic surgery, a burden on the body due to the surgery is less and recovery after the surgery is faster than in laparotomy surgery or open-chest surgery.

By the way, in the laparoscopic surgery, due to dirt and the like on a lens and the like of the endoscope scope, work is repeated several times in which the endoscope scope is pulled out, and the dirt on the lens and the like are cleaned, and then the endoscope scope is reinserted. On this occasion, when trying to reproduce the same angle of view as before the scope is pulled out, the work relies on memory of a person, and becomes a difficult work.

Therefore, a technology has been devised for assisting in obtaining a position that has been captured before the endoscope scope is pulled out (see Patent documents 1, 2).

In addition, a technology has been devised for finding out the affected part seen before (see Patent document 3).

CITATION LIST

Patent Document

Patent document 1: Japanese Patent Application Laid-Open No. 2014-079377
Patent document 2: Japanese Patent Application Laid-Open No. 2014-083289
Patent document 3: Japanese Patent Application Laid-Open No. 2012-170774

SUMMARY OF THE INVENTION

Problems to be Solved by the Invention

The technologies of Patent documents 1 to 3 described above have been capable of assisting in obtaining the position seen, or finding out the affected part seen before; however, it has not been possible to find out a desired affected part, and further reproduce the angle of view of before the endoscope scope is pulled out, for example.

The present technology has been made in view of such a situation, and in particular assists with operation of the endoscope scope so that the angle of view of immediately before the endoscope scope is pulled out can be captured when the endoscope scope is pulled out for cleaning and the like and then reinserted.

Solutions to Problems

An endoscope apparatus of one aspect of the present technology includes: a recording unit for recording an image captured by an image capture unit of an endoscope scope having the image capture unit for capturing an image at a tip of an insertion portion to be inserted into a body cavity; an assist display control unit for generating as an assist image an image synthesized from information indicating an angle of view of any selected image selected from images recorded in the recording unit and information indicating an angle of view of a captured image that is an image currently captured by the image capture unit; and a display unit for displaying the assist image.

The information indicating the angle of view of each of the selected image and the captured image can be a mark indicating positions of a center and corners of a corresponding one of the selected image and the captured image.

The information indicating the angle of view of each of the selected image and the captured image can be an image obtained by edge extraction from a corresponding one of the selected image and the captured image.

The endoscope apparatus can be configured to further include: a feature value detection unit for detecting a feature value of the captured image; and a matching unit for detecting an amount of deviation by matching based on a feature value difference between the captured image and the selected image, wherein the assist display control unit displays information indicating that the assist image cannot be displayed on the display unit when the amount of deviation is greater than a predetermined value.

The endoscope apparatus can be configured such that the matching unit detects a forceps in the captured image and selected image, and the assist display control unit hides the forceps detected by the matching unit and generates the assist image.

The endoscope apparatus can be configured to further include: a feature value detection unit for detecting a feature value of the captured image; and a recording control unit for recording the captured image in the recording unit in accordance with a change of the feature value, wherein the recording control unit adds an index to the captured image and records the image in the recording unit when a feature value difference that is a difference of a feature value between consecutive images in time series of the captured image is greater than a predetermined value.

The endoscope apparatus can be configured such that the feature value, when the image is divided into a plurality of blocks, includes a sum of absolute differences between adjacent pixels and a sum total of luminance values in each of the blocks, and a sum of absolute differences between adjacent pixels and a sum total of luminance values of a central block of the blocks.

The endoscope apparatus can be configured such that the assist display control unit displays a list of images each to which the index is added, of images stored in the recording unit when display of the assist image is requested.

The endoscope apparatus can be configured such that the assist display control unit sets an image selected from the list of the images each to which the index is added, as the selected image.

The endoscope apparatus can be configured such that the recording control unit deletes an image in order from the oldest to the newest of images recorded in the recording unit, and records the captured image in the recording unit, when a remaining capacity of a storage capacity of the recording unit is less than a predetermined value.

The endoscope apparatus can be configured such that the recording control unit records a feature value of the captured image and information indicating whether or not display of the assist image is requested, in association with a time code, in addition to the captured image, when recording the captured image in the recording unit.

The endoscope apparatus can be configured to further include: a reproducing unit for reproducing an image of the images recorded in the recording unit correspondingly to the time code, wherein the image is an image at a timing at which display of the assist image is not requested and the feature value difference between images at consecutive different timings is less than a predetermined value.

A method for operating an endoscope of one aspect of the present technology includes: recording an image captured by an image capture unit of an endoscope scope having the image capture unit for capturing an image at a tip of an insertion portion to be inserted into a body cavity; generating as an assist image an image synthesized from information indicating an angle of view of any selected image selected from images recorded in the recording unit and information indicating an angle of view of a captured image that is an image currently captured by the image capture unit; and displaying the assist image.

A program of one aspect of the present technology causes a computer to function as: a recording unit for recording an image captured by an image capture unit of an endoscope scope having the image capture unit for capturing an image at a tip of an insertion portion to be inserted into a body cavity; an assist display control unit for generating as an assist image an image synthesized from information indicating an angle of view of any selected image selected from images recorded in the recording unit and information indicating an angle of view of a captured image that is an image currently captured by the image capture unit; and a display unit for displaying the assist image.

In one aspect of the present technology, an image is recorded captured by an image capture unit of an endoscope apparatus having the image capture unit for capturing an image at a tip of an insertion portion to be inserted into a body cavity, an image is generated as an assist image synthesized from information indicating an angle of view of a selected image selected from an image recorded in the recording unit and information indicating an angle of view of a captured image that is an image currently captured by the image capture unit, and the assist image is displayed.

The endoscope apparatus of one aspect of the present technology may be an independent apparatus, and may be a block that functions as the endoscope apparatus and each of the endoscope apparatuses.

Effects of the Invention

With one aspect of the present technology, it is possible to assist with operation of the endoscope scope so that the angle of view of immediately before the endoscope scope is pulled out can be captured when the endoscope scope is pulled out for cleaning and the like and then reinserted.

MODE FOR CARRYING OUT THE INVENTION

<Summary of Endoscope Apparatus>

Figure 1:
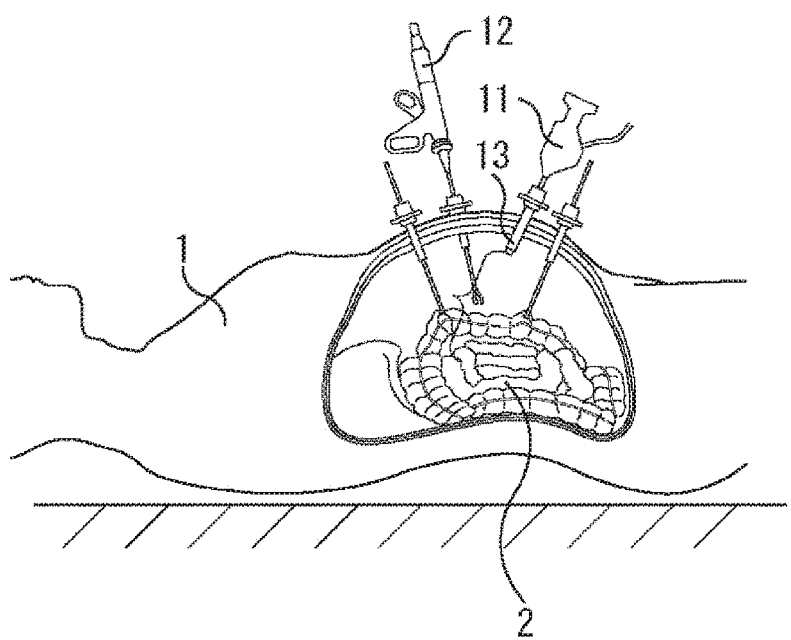
FIG. 1 is a diagram illustrating a summary of laparoscopic surgery.

FIG. 1 is a diagram for describing a summary of an endoscope apparatus to which the present technology is applied.

The endoscope apparatus is used in laparoscopic surgery performed instead of conventional laparotomy surgery at a medical site in recent years.

That is, as illustrated in FIG. 1, in laparoscopic surgery, when laparotomy surgery is performed, for example, instead of cutting an abdominal wall 1 to perform laparotomy that is conventionally performed, several perforating tools each referred to as a trocar 13 are attached to the abdominal wall, and a laparoscope (hereinafter, also referred to as an endoscope apparatus or an endoscope) 11, and a forceps 12 that is a treatment tool are each inserted into a body from a hole provided in the trocar 13. Then, while an image of an affected part (tumor and the like) 2 video-captured by the endoscope scope 11 is seen in real time, treatment is performed such as excision of the affected part 2 by a treatment tool such as the forceps 12.

Incidentally, since a tip part of the endoscope scope 11 is dirtied by bleeding and the like, it is repeated that the scope is pulled out from the trocar 13 and cleaned and then reinserted, several times during surgery.

In the straight rod-shaped endoscope scope 11 as illustrated in FIG. 1, a head part 71 (FIG. 3) is held by an operator, assistant, endoscope operator, robot, or the like, and operation is performed of changing an angle of view by holding the head part 71.

On this occasion, when the endoscope scope 11 is reinserted, operation is necessary for returning the angle of view to an image capture state of before the endoscope is pulled out, that is, the angle of view captured before the endoscope is pulled out; however, conventionally, there has been a case in which it takes time for returning the angle of view since the operation only has relied on sense of the operator, assistant, or endoscope operator.

Therefore, the endoscope apparatus to which the present technology is applied includes a function for assisting with the operation for returning the angle of view to an immediately preceding image capture state (image capture angle of view) at the time of reinsertion of the endoscope scope 11. Thus, it is possible to return the angle of view quickly to the original angle of view, at the time of reinsertion of the laparoscope scope, and to shorten surgery time as a whole.

<One Embodiment of the Endoscope Apparatus to which the Present Technology is Applied>

Figure 2:
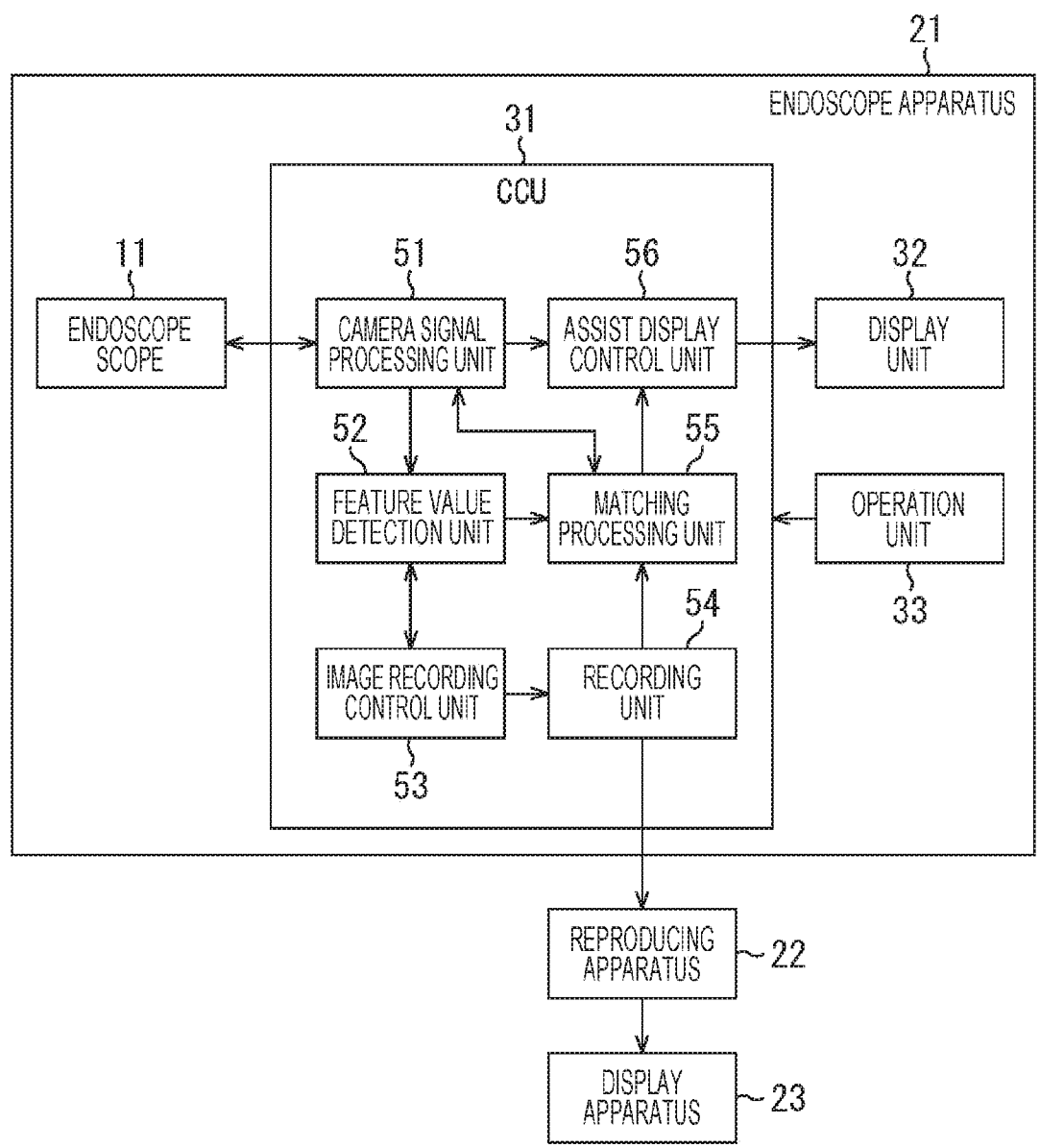
FIG. 2 is a diagram for describing a configuration of an endoscope apparatus.

FIG. 2 illustrates a configuration example of one embodiment of the endoscope apparatus to which the present technology is applied.

An endoscope apparatus 21 of FIG. 2 includes the endoscope scope 11, a color control unit (CCU) 31, a display unit 32, and an operation unit 33. In addition, in order to reproduce an image captured by the endoscope apparatus 21, a reproducing apparatus 22, and a display apparatus 23 may be provided separately, and the endoscope apparatus may be configured to include these apparatuses.

The CCU 31 functions as an image processing apparatus, and receives an image captured by the endoscope scope 11, and sequentially records the image, and generates information for assisting in starting image capture with the angle of view of immediately before the endoscope scope 11 is pulled out when the endoscope scope 11 is reinserted, and displays the information on the display unit 32.

More specifically, the CCU 31 includes a camera signal processing unit 51, a feature value detection unit 52, an image recording control unit 53, a recording unit 54, a matching control unit 55, and an assist display control unit 56.

The camera signal processing unit 51 performs demosaic processing to an image signal supplied from the endoscope scope 11, for example, an image supplied as an RGB signal, and performs signal processing such as noise reduction, and gradation control, and generates an image signal having a predetermined frame rate. In addition, as will be described later, the image signal includes an aperture, a shutter speed, a focal length, an operating state of an optical system (movement position of a lens), and Exif information in addition to information indicating a light source type such as normal light or special light generated by a light source apparatus 73 when the endoscope scope 11 performs image capture, and the image signal is output together with those pieces of information to the feature value detection unit 52 and the assist display control unit 56.

The feature value detection unit 52 calculates a feature value that can be compared with that of another image for each image, and outputs the feature value together with the image signal to the image recording control unit 53.

For example, the feature value detection unit 52 divides an input image into five divisions by five divisions respectively in the horizontal direction and the vertical direction, totally into 25 blocks, and obtains a difference between adjacent pixels for each of the blocks, and calculates a value for each of the blocks, such as a maximum value or an average value, as the feature value obtained for each of the blocks. Alternatively, the feature value detection unit 52 divides the input image into five divisions by five divisions respectively in the horizontal direction and the vertical direction, and obtains a difference between adjacent pixels for the central block of the divided blocks, and calculates a value of the central block, such as a maximum value or an average value, as the feature value.

Further, the feature value detection unit 52 may extract information such as a light source type, an aperture, a shutter speed, a focal length, an operating state of an optical system (movement position of a lens), and Exif information as the feature value, and may use a combination thereof as the feature value.

The image recording control unit 53 records information such as the image signal, the feature value, and presence of assist display sequentially in the recording unit 54 in association with the time stamp. On this occasion, the image recording control unit 53 monitors a recordable remaining capacity, and sequentially deletes the information corresponding to the oldest time stamp and records the latest information by overwriting the oldest information, when the remaining capacity of the recording unit 54 is less than a predetermined amount.

In addition, when detecting a scene change indicating that the endoscope scope 11 is pulled out or occurrence of blood, smoke, or dirt that is a characteristic change in the image, the image recording control unit 53 adds an index and performs recording to the recording unit 54 by controlling the matching processing unit 55 and performing matching of the current image and the immediately preceding image by using the feature value.

More specifically, for example, in a case in which the image is divided into 25 blocks, and when the information is included such as the average value of the difference between adjacent pixels for each of the blocks, the matching processing unit 55 obtains as a feature value a difference of the average values of the difference between adjacent pixels between images consecutive in time series for each of the blocks, and regards that any change has occurred in the image when a significant change has occurred in at least one block or more. That is, the matching processing unit 55 regards that a phenomenon occurred such as a scene change, blood, smoke, or dirt. In such a case, the image recording control unit 53 records image information in association with the timestamp, with the index added.

In addition, when it is instructed to perform the assist display, the matching processing unit 55 first reads as a list the images each to which the index is added, outputs the list to the assist display control unit 56, and displays on the display unit 32 composed of a liquid crystal display (LCD) and the like, as a list of selected images each of which is desired to be selected as the image of the angle of view that can be displayed at the time of reinsertion of the endoscope scope 11.

When the operation unit 33 is operated and one of the selected images in the list is selected, the matching processing unit 55 outputs an image based on the selected image selected to the assist display control unit 56. The assist display control unit 56 generates an assist image from which a direction and distance of one image deviated from that of the other image can be recognized by using the image that is selected as the selected image and serves as a reference, and an image supplied from the camera signal processing unit 51, and displays the assist image on the display unit 32. With such an assist image, the direction and distance of deviation between the selected image that serves as a reference and the image currently captured is displayed on the display unit 32.

On this occasion, the assist display control unit 56 performs edge extraction filter processing to each of the selected image and the current image being captured, and generates an assist image in which the images are displayed to overlap each other so that subject's edge portions of the respective images can be recognized as different images such as a dotted line and a solid line, or red display and blue display. With such an assist image, a user is assisted in obtaining the angle of view of the desired selected image, by recognizing the direction and distance of deviation of the angle of view of the current image with respect to the angle of view of the desired selected image.

The reproducing apparatus 22 reproduces the image on the basis of the image information recorded in the recording unit 54, and displays the image on the display apparatus 23 composed of the LCD and the like. Incidentally, the image displayed on the display apparatus 23 by the reproducing apparatus 22 is supposed to be reproduced after surgery, not the image during surgery.

<Configuration Example of Endoscope Apparatus>

Figure 3:
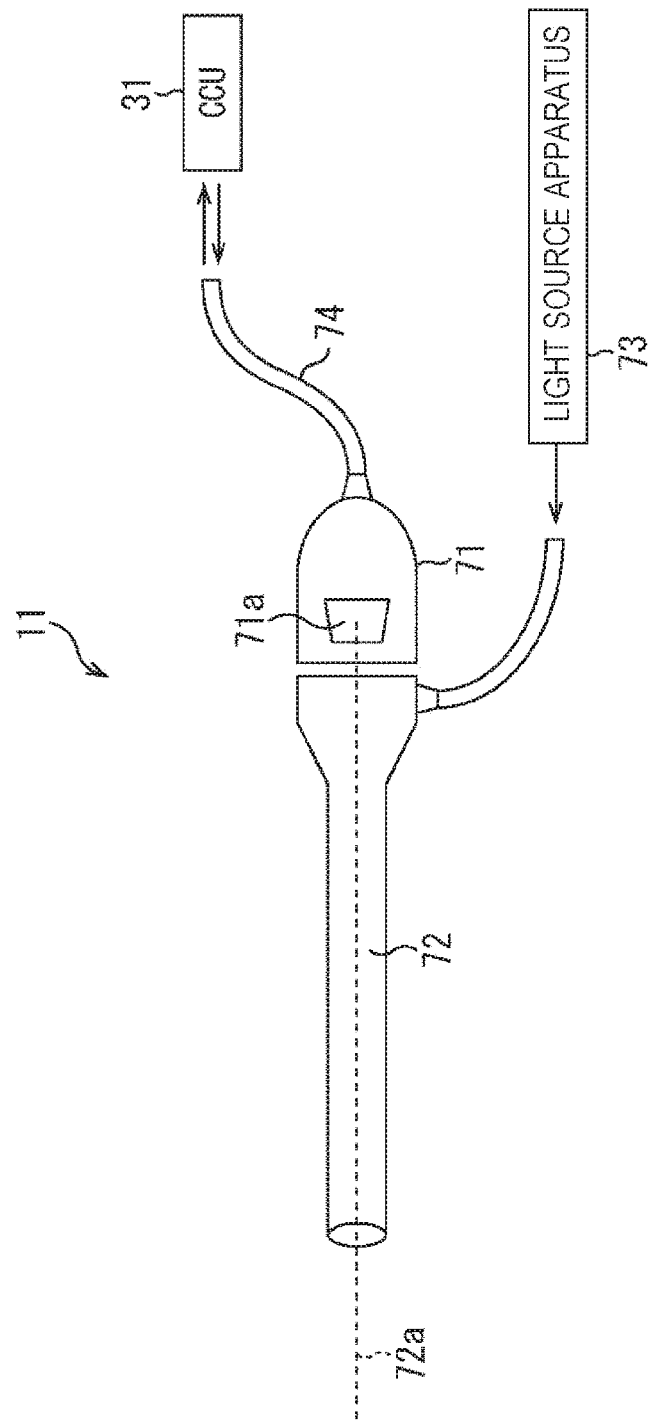
FIG. 3 is a diagram for describing the endoscope apparatus of FIG. 2.

Next, a configuration example of the endoscope scope 11 will be described with reference to FIG. 3.

The endoscope scope 11 includes a head part 71, a hard mirror (lens barrel) 72, a light source apparatus 73, and a cable 74. The head part 71 is configured to include an image capture device 71a including a complementary metal oxide semiconductor (CMOS), and captures an image of the affected part 2 via the hard mirror 72 to be inserted into an abdominal cavity via the trocar 13 (FIG. 1), and outputs the image as an image signal having a predetermined frame rate to the CCU 31 via the cable 74. Incidentally, description will be made for an example in which the endoscope scope 11 and the CCU 31 are connected together via the cable 74; however, the endoscope scope 11 and the CCU 31 may be connected together wirelessly, other than being connected together via the cable 74. In addition, the CCU 31 may be placed at a location far from an operating room, and may be connected to the endoscope scope 11 via a network such as an in-house LAN or the Internet. The CCU 31 and the display unit 32 are connected together similarly.

The hard mirror (lens barrel) 72 is the one that transmits an image of the affected part 2 and the like in the abdominal cavity to the image capture device 71a optically along a lens barrel axis 72a by using a plurality of times of relay lens systems and, in particular, whose main body is rod-shaped and whose insertion portion into the trocar 13 is hard. Incidentally, the hard mirror 72 that serves as a lens barrel does not necessarily have to be hard, and may be substituted by a soft lens barrel.

The light source apparatus 73 generates light as a light source, and emits the light to the affected part 2 via the hard mirror 72. At this time, the light source apparatus 73 can be a light source of various types of light by switching the wavelength of the light as the light source, and is capable of generating special light by which lesion is easily seen depending on the lesion, for example. At this time, information indicating the light source type selected in the light source apparatus 73 is supplied to the CCU 31 via the cable 74.

<Assist Processing>

Next, assist processing by the endoscope apparatus 21 of the present technology will be described with reference to a flowchart of FIG. 4.

In step S11, the matching processing unit 55 reads an operating state of the light source apparatus 73 from the endoscope scope 11 via the camera signal processing unit 51, and the cable 74, and reads an image capture mode. For example, the image capture mode is recognized as a normal mode when the light source apparatus 73 emits normal white light, and is recognized as a special light mode when the special light is emitted.

In step S12, the matching processing unit 55 extracts a selected image recorded in a state corresponding to the current image capture mode, of the image information recorded in the recording unit 54, and outputs the selected image to the assist display control unit 56. The assist display control unit 56 displays these selected images as a list on the display unit 32, and displays an image prompting selection of an image to be displayed as assist display. Incidentally, the image displayed here is an image to which an index is added at a timing at which any change has occurred such as pulling out of the endoscope scope, bleeding, smoke emission, occurrence of dirt, of the image captured by immediately preceding operation. Incidentally, recording processing for the captured image signal will be described later in details with reference to a flowchart of FIG. 8.

In step S13, the matching processing unit 55 determines whether or not the operation unit 33 is operated and any one of the selected images is selected, and repeats similar processing until the selected image is selected. Then, in step S13, when the operation unit 33 is operated and any one of the selected images is selected, the processing proceeds to step S14.

In step S14, the matching processing unit 55 reads the selected image selected by the operation unit 33 operated, from the recording unit 54, and outputs the selected image to the assist display control unit 56. The assist display control unit 56 displays the selected image selected, on the display unit 32, and displays an image for inquiring necessity of assist display.

Incidentally, since operation is often repeated during normal endoscopic surgery after the endoscope scope 11 is pulled out via the trocar 13, the tip part of the hard mirror 72 is cleaned, and reinserted into the trocar 13, a selected image may be set as a default selected image, which is an image of immediately before the endoscope scope 11 is pulled out from the trocar 13 and a stable image. In this way, it is possible to achieve operation for assisting in obtaining the state of immediately before the endoscope scope 11 is pulled out from the trocar 13, when the endoscope scope 11 is pulled out and then reinserted, without performing operation for selecting the selected image.

In step S15, the matching processing unit 55 determines whether or not the operation unit 33 is operated and it is instructed to perform the assist display, and repeats similar operation until it is instructed to perform the assist display. Then, in step S15, when the operation unit 33 is operated and it is instructed to perform the assist display, the processing proceeds to step S16.

In step S16, the matching processing unit 55 instructs the camera signal processing unit 51 to capture an image by the endoscope scope 11. In response to this, the camera signal processing unit 51 causes the image capture device 71a provided to the head part 71 in the endoscope scope 11 to capture an image.

In step S17, the camera signal processing unit 51 performs camera signal processing to the image signal captured by the image capture device 71a, and outputs the image signal to the feature value detection unit 52 and the assist display control unit 56.

In step S18, the feature value extraction unit 52 extracts the feature value on the basis of the image signal input, and outputs the image signal together with the feature value extracted to the matching processing unit 55.

In step S19, the matching processing unit 55 performs matching processing on the current image and the selected image, and detects the corresponding position of each of the images. More specifically, the matching processing unit performs block matching in the selected image on a block including a plurality of pixels within a predetermined range near the center in the current image, and detects the corresponding position. Incidentally, a specific matching processing method may be any method as far as it is possible to detect the corresponding position of each of the current image and the selected image.

In step S20, the matching processing unit 55 calculates an amount of deviation between the current input image and the selected image. For example, the matching processing unit 55 may obtain as the amount of deviation a distance between central positions of the images of when the current image and the selected image are superimposed on each other so that the mutually corresponding positions detected by the matching processing described above overlap each other.

In step S21, the matching processing unit 55 determines whether or not the amount of deviation is within an allowable range. That is, when the amount of deviation is too large, there is a possibility that it becomes impossible to display the current input image in the full screen and superimpose and display the selected image, and the assist image cannot be configured appropriately, when the assist image to be described later is displayed. Therefore, the matching processing unit 55 determines whether or not the assist image can be appropriately displayed on the basis of whether or not the amount of deviation is within the allowable range.

In step S21, for example, when it is determined that the amount of deviation is not within the allowable range, in step S22, the matching processing unit 55 supplies information indicating that the amount of deviation is not within the allowable range and the assist display cannot be performed, to the assist display control unit 56. On the basis of the information, the assist display control unit 56 displays the information indicating that the amount of deviation is not within the allowable range and the assist display cannot be performed, on the display unit 32.

On the other hand, in step S21, when the amount of deviation is within the allowable range, in step S23, the matching processing unit 55 detects a treatment tool 3 such as a forceps from each of the current input image and the selected image.

Then, in step S24, the matching processing unit 55 hides display of the treatment tool 3 such as the forceps detected from each of the current input image and the selected image.

That is, for example, when there is the forceps 12 illustrated in FIG. 1 in the image, there is a possibility that a surgical field near the affected part 2 becomes small. Therefore, only when the assist image is displayed, the forceps 12 is prevented from being displayed in the image until the display of the assist image becomes unnecessary. More specifically, the matching processing unit 55 stores the color and shape of the forceps 12 in advance, and performs displaying by replacing a part corresponding to the color and shape with a pixel signal that is captured at another timing and becomes a corresponding position by matching. In this way, it is possible to achieve the assist image in which the processing tool such as the forceps 12 and the like are not displayed.

In step S25, the matching processing unit 55 generates the assist image by displaying the pieces of information respectively indicating the angle of views of the selected image and the current input image in which the forceps 12 is hidden to overlap each other at the corresponding position, and supplies the assist image to the assist display control unit 56. The assist display control unit 56 displays the assist image supplied from the matching processing unit 55 on the display unit 32.

Figure 5:
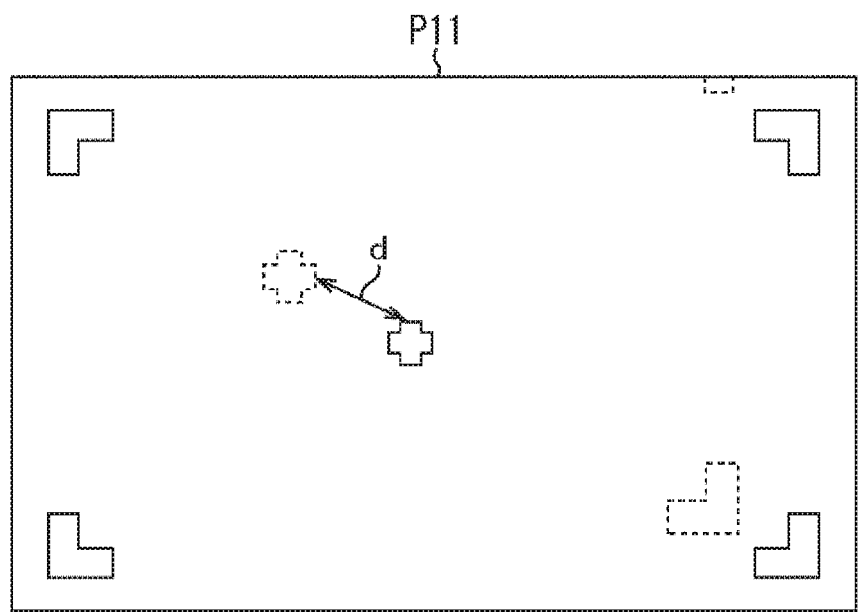
FIG. 5 is a diagram for describing an assist image.

At this time, for example, as illustrated in an assist image P11 of FIG. 5, when the input image and the selected image are displayed to overlap each other, marks each indicating a center position and a frame that are pieces of information of the angle of view are displayed together, whereby the deviation between the input image and the selected image can be recognized in the image. In this way, the direction and distance of the deviation to the desired angle of view can be presented, so that it is possible to appropriately assist in obtaining the desired angle of view. That is, in the assist image P11 of FIG. 5, the mark indicating the center and corners of the frame of the input image is displayed by the solid line, and the mark indicating the central position (center position) and corners of the frame of the selected image is indicated by the dotted line. That is, in FIG. 5, the distance indicated by an arrow d is the amount of deviation, so that it is possible to recognize the direction and distance to be corrected at a glance from the assist image. Incidentally, the arrow d of FIG. 5 is added for describing the amount of deviation and the direction, and is not displayed.

Figure 6:
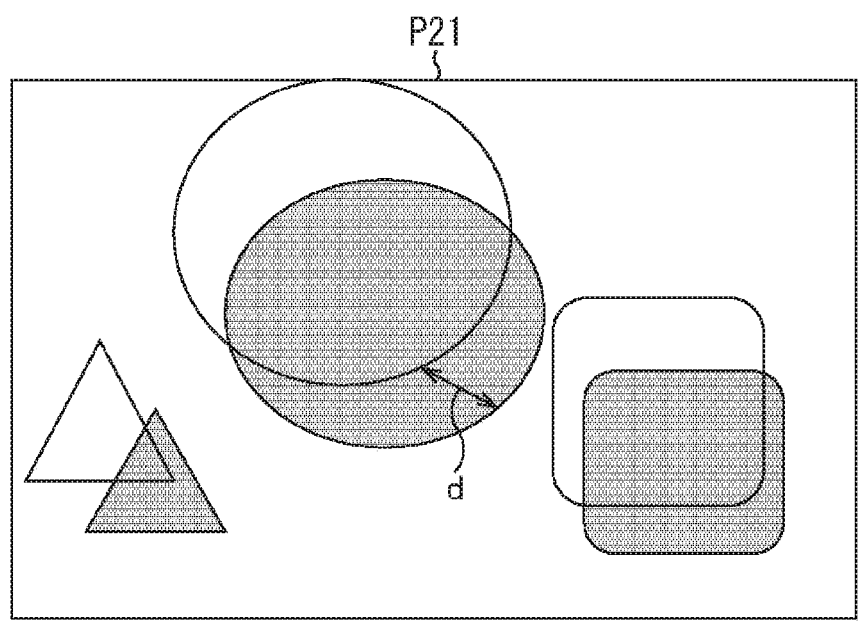
FIG. 6 is a diagram for describing another assist image.

Further, as illustrated in an assist image P21 of FIG. 6, the matching processing unit 55 may perform edge extraction processing to each of the input image and the selected image, and display only their edge images to overlap each other, to recognize the direction and distance of the deviation. Here, in the assist image P21 of FIG. 6, the input image is the image in which the range surrounded by the edge is black, and the selected image is the image in which the range surrounded by the edge is white. Incidentally, similarly to FIG. 5, the arrow in FIG. 6 also represents an example indicating the amount of deviation and the direction, and is not actually displayed.

Figure 7:
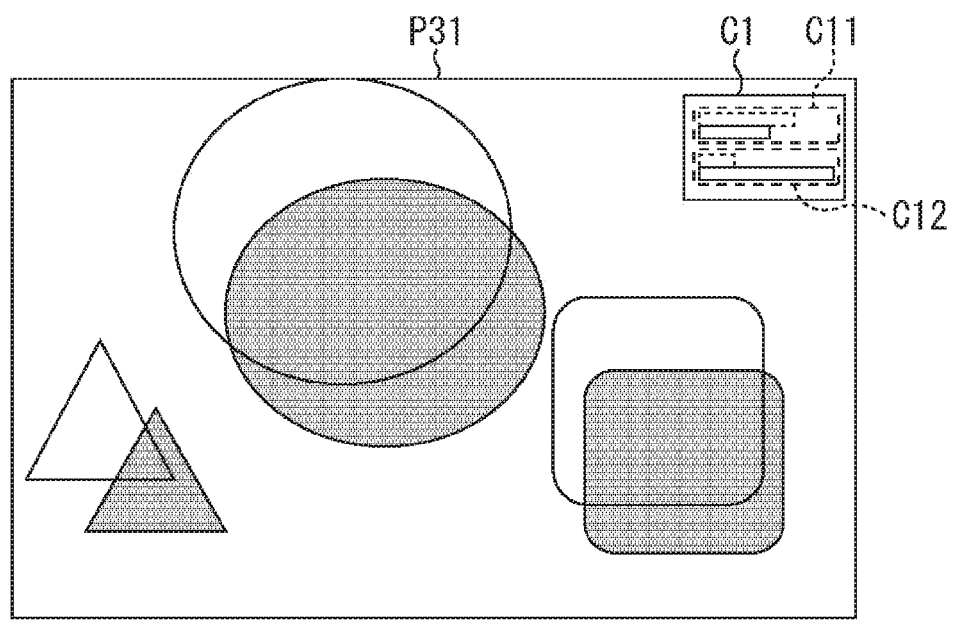
FIG. 7 is a diagram for describing yet another assist image.

In addition, as illustrated in an assist image P31 of FIG. 7, a feature value comparative information display field C1 may be provided at the upper right part of the image. In the upper part of the feature value display field C1 of FIG. 7, a display field C11 is provided in which bar graphs are displayed side by side for comparing sum total of luminance values in each of blocks of when the input image and the selected image are each divided into five divisions by five divisions respectively in the horizontal direction and the vertical direction, totally into 25 divisions, for example. In addition, in the lower part of the feature value display field C1 of FIG. 7, a display field C12 is provided in which bar graphs are displayed side by side for comparing the maximum values of the difference between adjacent pixels in each of the blocks, for example.

With the feature value display field C1 provided, when the endoscope scope 11 is operated and the angle of view is changed so that edge portions of the input image and the selected image overlap each other while the assist image P31 is seen, and the edge portions accurately overlap each other, the pieces of information of the feature value also coincide with each other. Accordingly, the user operates the endoscope scope 11 so that the edge portions overlap each other, and the pieces of information of the feature value coincide with each other, thereby being capable of adjusting the state of the input image to the same angle of view as the selected image accurately. In particular, even in a case of the image in which confirmation of matching is difficult only with the outline of the image, it is possible to perform operation more accurately by performing the operation so that the pieces of information coincide with each other of the feature value display field C1 in which the feature values of the input image and the selected image are compared and displayed.

Figure 4:
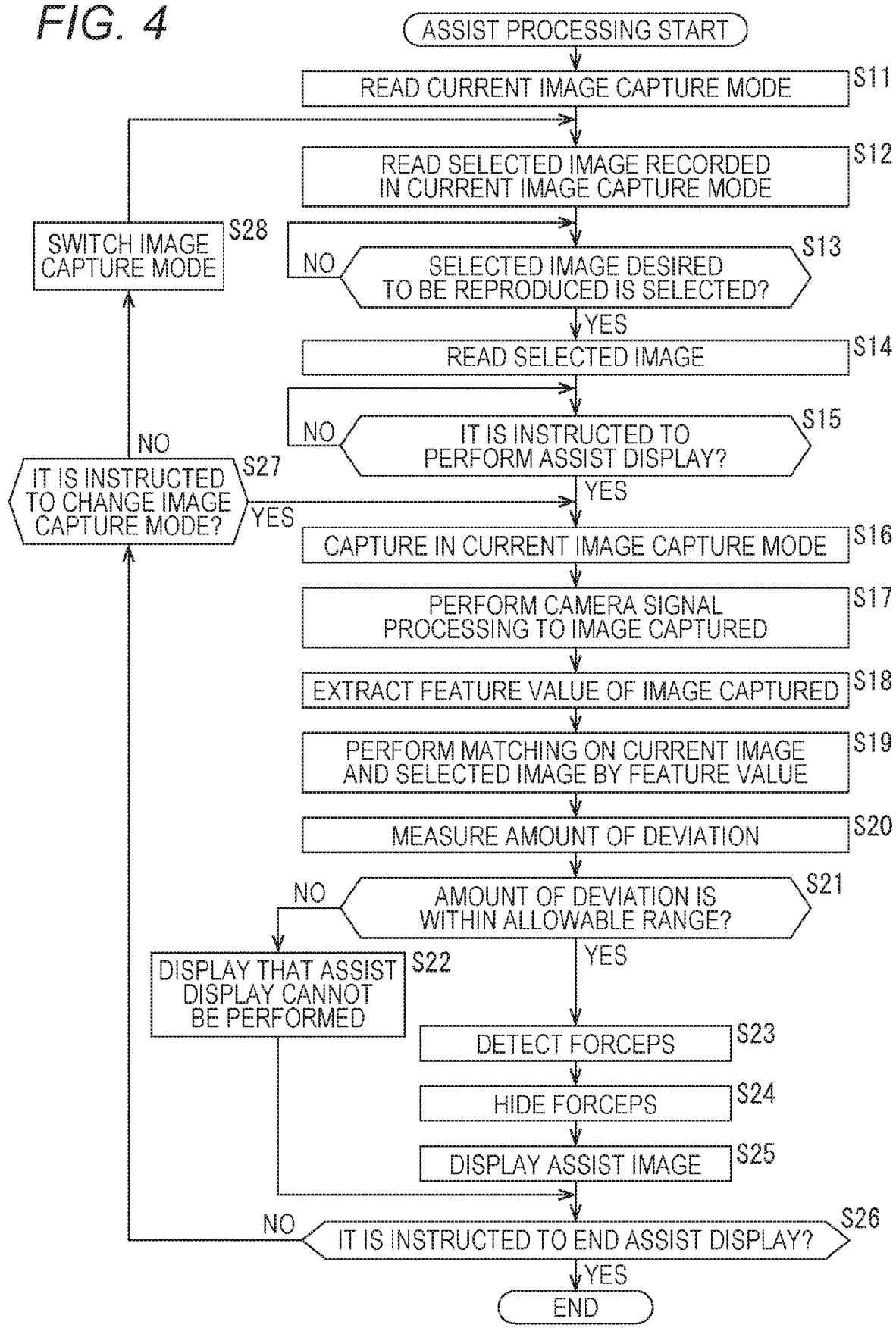
FIG. 4 is a flowchart for describing assist processing by the endoscope apparatus of FIG. 2.

Here, returning to description of FIG. 4.

In step S26, the camera signal processing unit 51 determines whether or not the operation unit 33 is operated and it is instructed to end the assist display, and when it is not instructed to end, the processing proceeds to step S27.

In step S27, the camera signal processing unit 51 determines whether or not it is instructed to change the image capture mode from the endoscope scope 11 via the cable 74. That is, it is determined whether or not it is instructed to change the image capture mode due to the fact that the light source apparatus 73 is operated and switched from the normal light to the special light, or the like. In step S27, when there is no change in the image capture mode, the processing returns to step S16. That is, when there is no change in the image capture mode, and it is not instructed to end, the processing in steps S16 to S27 is repeated.

In addition, in step S27, when it is determined that the image capture mode is switched, the processing proceeds to step S28.

In step S28, the camera signal processing unit 51 switches the image capture mode to an image capture mode supplied from the endoscope scope 11 via the cable 74, and the processing returns to step S12. That is, in this case, since the image capture mode is different, operation to select the selected image is necessary again.

Then, in step S26, when it is instructed to end, the processing is ended.

With the above processing, as far as it is instructed to display the assist image, by the operation of the endoscope scope 11, the images continue to be displayed to overlap each other in which the angle of view can be recognized of each of the input image around the affected part 2 captured by the image capture device 71a via the hard mirror 72, and the selected image selected of the selected images captured in advance, so that it is possible to assist in obtaining the angle of view similar to the selected image by moving or rotating in a certain amount and in a certain direction while changing the position and the image capture direction of the endoscope scope 11. In addition, it is possible to present the assist image for assisting in obtaining the state in which the angle of view of immediately before the endoscope scope 11 is pulled out can be captured surely for each time reinsertion is repeated, by setting the selected image to the image of immediately before the endoscope scope 11 is pulled out from the trocar 13, during surgery. In addition, during this time, the processing tool such as the forceps 12 is hidden, so that it is possible to make setting to the desired angle of view of the selected image further easier.

As a result, even when operation is repeated such that the endoscope scope 11 is pulled out from the trocar 13 and reinserted during surgery, it is possible to return the angle of view quickly to the angle of view captured immediately before the endoscope scope 11 is pulled out, or the desired angle of view, and it is prevented that the surgical time is prolonged only for returning the angle of view, and it is possible to shorten the surgical time, and accordingly reduce the burden on the body of the patient by the surgery.

<Recording Processing>

Figure 8:
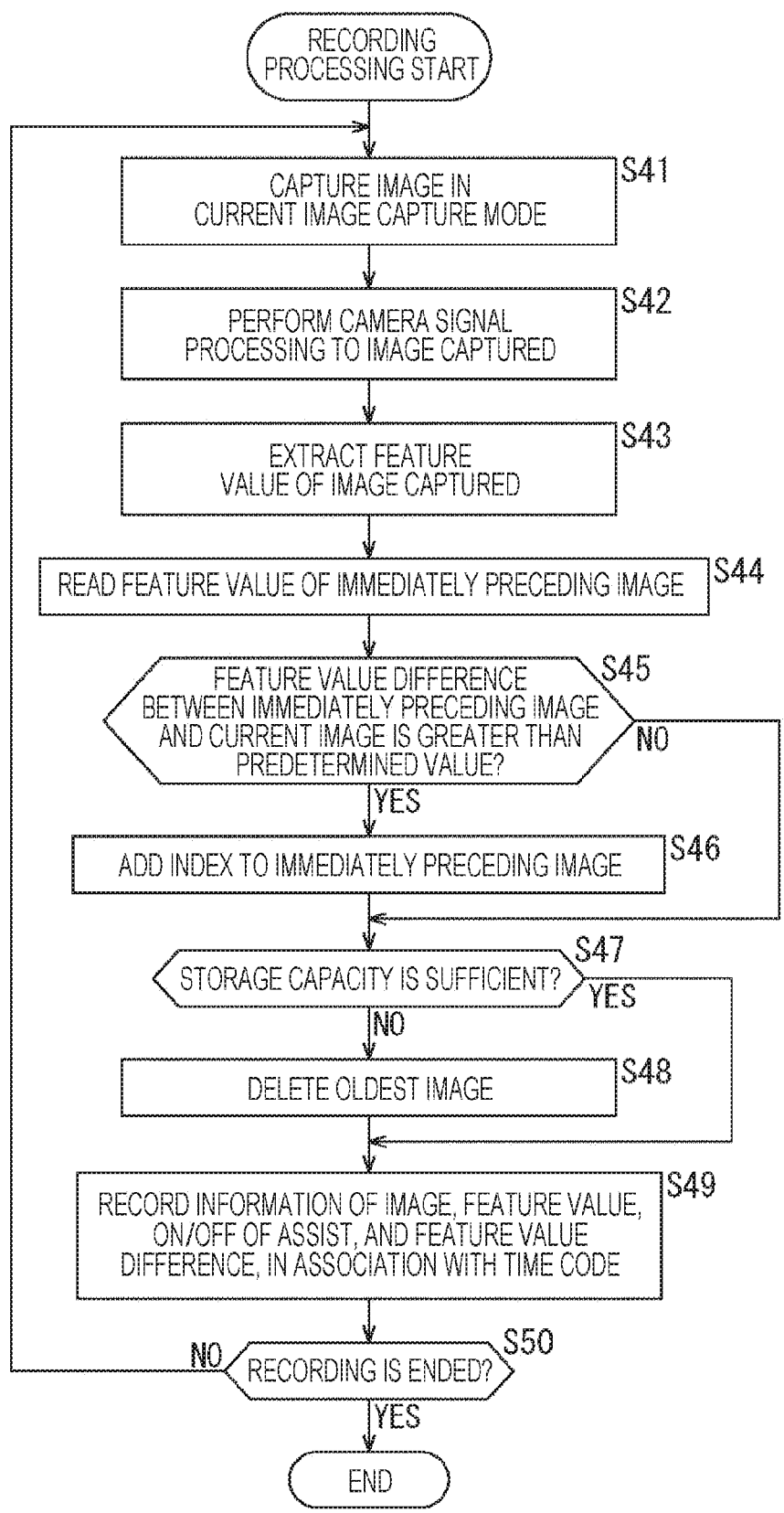
FIG. 8 is a flowchart for describing recording processing.

Next, recording processing will be described with reference to a flowchart of FIG. 8. Incidentally, operation is performed, in which the image used in the assist processing described above is based on the image recorded in the recording unit 54 by the recording processing that is executed in the background of the assist processing.

In step S41, the camera signal processing unit 51 acquires information of the image capture mode depending on the light emitted by the light source apparatus 73 supplied from the endoscope scope 11 via the cable 74.

In step S42, the camera signal processing unit 51 acquires as an input image an image signal of the affected part 2 to be captured from the image capture device 71a via the hard mirror 72 in the endoscope scope 11, performs various types of signal processing to the input image, and outputs the input image to the feature value detection unit 52.

In step S43, the feature value detection unit 52 detects the feature value from the input image supplied, and outputs the feature value together with the input image and the information of the image capture mode to the image recording control unit 53.

In step S44, the image recording control unit 53 reads the immediately preceding image signal and the feature value recorded in the recording unit 54.

In step S45, the image recording control unit 53 obtains a feature value difference that is a difference of the feature value between the input image and the immediately preceding image, and determines whether or not the feature value difference is greater than a predetermined threshold. More specifically, for example, when each image is divided into 25 blocks and the feature value is obtained for each block, the image recording control unit 53 obtains a sum of absolute differences of the feature value of each block as the feature value difference. In addition, when only the feature value of the central block is obtained, the image recording control unit 53 obtains an absolute difference of only the feature value as the feature value difference.

In step S45, for example, when it is determined that the feature value difference is greater than a predetermined value, it is regarded that there is some change between the captured images, and the processing proceeds to step S46.

In step S46, the image recording control unit 53 adds the index indicating that the image read is an image to be used as a selected image, to the immediately preceding image read.

On the other hand, in step S45, when it is determined that the feature value difference is less than the predetermined value, it is regarded that there is no change, and the processing in the step S46 is skipped, and the index is not added to the immediately preceding image.

That is, when the operation occurs such that the endoscope scope 11 is pulled out from the trocar 13, a significant change occurs between the consecutive images, whereby the feature value difference is greater than the predetermined value. In addition, also in a case in which bleeding, smoke emission, adhesion of dirt, and the like occur in the image, a change occurs between the images. For this reason, the image at a timing at which the feature value difference significantly changes indicates a timing at which a change occurs during surgery, and the index is added to the image of immediately before the timing at which the change occurs, whereby it is possible to use a stable image of immediately before the change occurs as a selected image.

In step S47, the image recording control unit 53 reads a remaining recording capacity of the recording unit 54, and determines whether or not there is a sufficient storage capacity. In step S47, for example, when it is determined that the storage capacity is not sufficient, in step S48, the image recording control unit 53 deletes image information having the oldest time code of the image information stored in the recording unit 54. That is, the capacity of the recording unit 54 is adjusted so that the most recent highly important image information can be recorded. On this occasion, depending on the capacity to be recorded, the oldest image information and the second oldest image information may be both deleted, if necessary. Incidentally, in step S47, when it is regarded that there is sufficient storage capacity, the processing in step S48 is skipped.

In step S49, the image recording control unit 53 records the information of the input image, the image capture mode, the feature value, and on or off of the assist image, and, if necessary, the feature value difference from the immediately preceding image together, in the recording unit 54 in association with the time code.

In step S50, the camera signal processing unit 51 determines whether or not recording is ended on the basis of whether or not there is the next image, or on the basis of on/off of the operation, and when the recording is not ended, the processing returns to step S41. Then, in step S50, when it is regarded that the recording is ended, the processing is ended.

With the above processing, it is possible to record the image captured by the image capture device 71a of the endoscope scope 11 to which the information of the input image, the image capture mode, the feature value, and on or off of the assist image, the feature value difference, and the index are added, in the recording unit 54 in association with a time code.

With this operation, since the index is added to the image that is an image at a timing that should be noted during surgery and is the stable image of immediately before the change occurs, on the basis of the index, the selected images are set, displayed as a list, and made to be selectable, whereby it is possible to make it easy to select the selected image that is a reference of the assist image, in the assist processing.

<Reproducing Processing>

Next, reproducing processing will be described of the image recorded in the recording unit 54 in the CCU 31 in the endoscope apparatus 21 by the reproducing apparatus 22, with reference to a flowchart of FIG. 9. Incidentally, the above assist processing, and the recording processing are each operation of when the endoscope scope 11 in the endoscope apparatus 21 is used; however, the reproducing processing can be operated after surgery, in addition to processing during surgery.

In step S71, the reproducing apparatus 22 sets a reproducing start position to be set by a time code counter TC set by an operation button or a remote controller not illustrated.

In step S72, the reproducing apparatus 22 accesses the recording unit 54, and determines whether or not the image information recorded in association with the time code counter TC set is in a state in which display of the assist image is off, and the feature value difference is small.

That is, a timing at which the display of the assist image is off can be said that it is a timing at which image capture is already being performed with the endoscope scope 11 in an angle of view desired by the user who is an operator.

In addition, a timing at which the feature value difference is small can be said that it is a timing at which a change of the state is small in the image of the affected part 2 during surgery.

Accordingly, the fact that it is in both states can be considered that it is a timing at which the operator, endoscope operator, robot, or the like is performing surgery without abnormality. Therefore, in such a case, in step S73, the reproducing apparatus 22 reproduces the image of the time code counter TC, and displays the image on the display apparatus 23.

On the other hand, a timing at which the assist image is on can be said that it is a timing at which image capture is being performed with the endoscope scope 11 in an angle of view not desired by the user who is the operator.

In addition, a timing at which the feature value difference is large can be said that it is a timing at which the change of the state is large in the image of the affected part 2 during surgery, for example, any change is occurring such that the endoscope scope 11 is pulled out.

Accordingly, the fact that it is also in one of the states can be considered that it is a timing at which the operator, endoscope operator, or robot is not performing surgery. Therefore, in such a case, the processing in step S73 is skipped, and reproducing of the image of the time code TC is skipped.

In step S74, the reproducing apparatus 22 determines whether or not the reproducing is ended, and when the reproducing is not ended, in step S75, the time code counter TC is incremented by one, and the processing returns to step S72. Then, the processing in steps S72 to S75 is repeated until the reproducing is ended, and only the image at a timing at which surgery is being performed is displayed, and reproducing the image in which the endoscope scope 11 is being pulled out is skipped.

Then, in step S74, when it is regarded that it is instructed to end the reproducing, the processing is ended.

Figure 10:
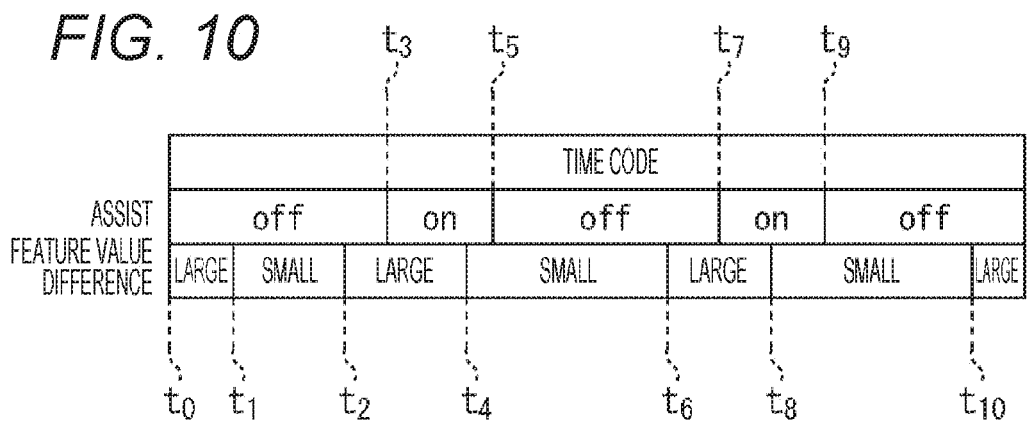
FIG. 10 is a diagram for describing reproducing processing.

That is, in a case as illustrated in FIG. 10, when reproducing is started along the time code in the figure, from time t0 to t1, from the fact that the assist image is off but change of the feature value is large, there is a high possibility that an inappropriate image difficult to be viewed, such as an image with a large blur, is not captured, so that the reproducing apparatus 22 performs processing not to display the image on the display apparatus 23, and from time t2 to t3, from the fact that the assist image is off and the feature value difference is small, there is a high possibility that a normal surgery scene with little blur is captured, so that the reproducing apparatus 22 displays the image at such timing on the display apparatus 23.

In addition, from the fact that the feature value difference is large from time t2 to t4, and the assist image is on from time t3 to t5 which partially overlap therewith, it is considered that the endoscope scope 11 is pulled out at time t2, reinserted at time t3, and accordingly the assist image is on.

Further, the feature value difference is small at time t4 and later, and further, the assist image is off at time t5. That is, it is considered that the feature value difference is small since angle of view setting is completed with the assist image at time t4, and the assist image is off at time t5. In such a case, the reproducing apparatus 22 does not display the image on the display apparatus 23 from time t2 to t5, and displays on the display apparatus 23 at time t5 and later.

Further, this is considered to be similar also at time t6 and later. That is, since the feature value difference is large at time t6, the endoscope scope 11 is pulled out, and after that, the assist image is on at time t7 when the endoscope scope 11 is reinserted. Then, setting of the angle of view is completed at time t8, whereby the feature value difference is small, and the assist image is off at time t9. As a result, in this case, from time t6 to t9, the reproducing apparatus 22 does not output the image to the display apparatus 23, and skips. Then, from time t9 to t10, the reproducing apparatus 22 outputs and displays the reproducing image on the display apparatus 23.

Incidentally, FIG. 10 illustrates from the top the time code, on or off of the assist image, and large or small of the feature value difference.

With the above processing, when the reproducing image for confirming surgery is displayed on the display apparatus 23 after the surgery, it is possible to perform the display by thinning out the image at a timing at which the endoscope scope 11 is pulled out, so that it is possible to display the image efficiently edited.

Figure 9:
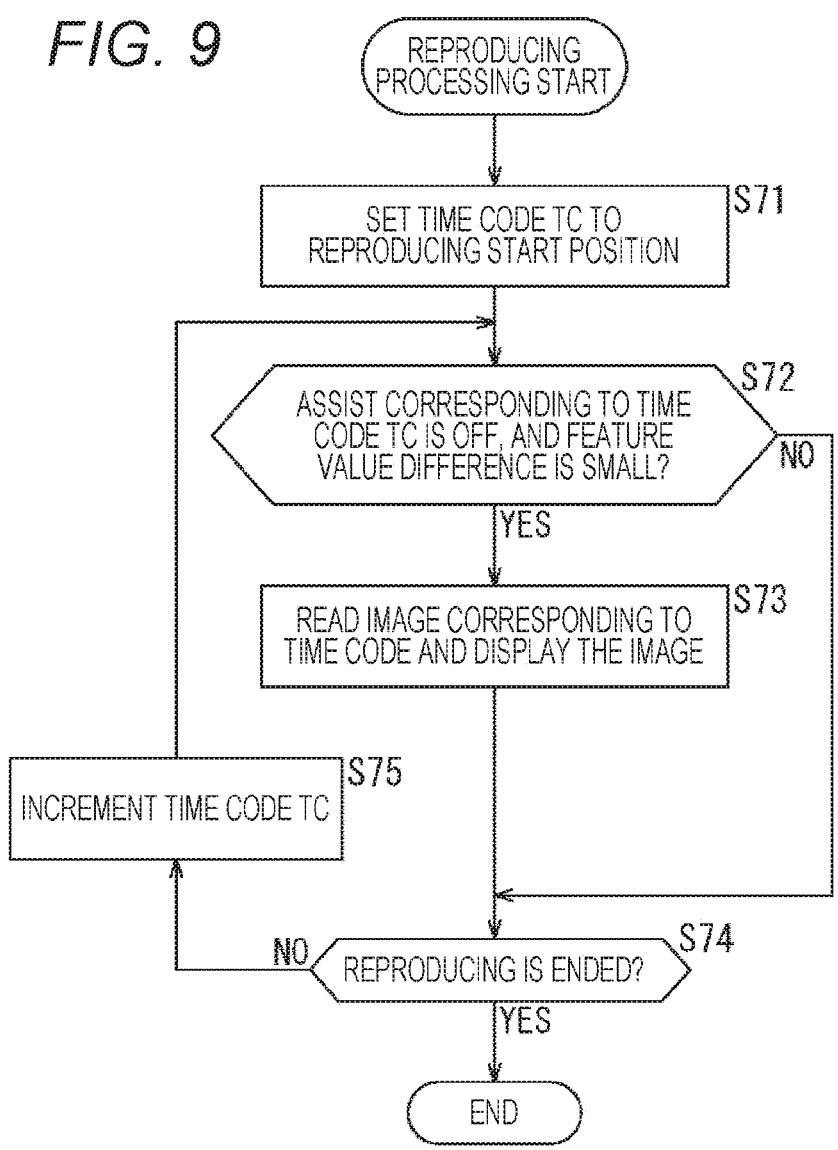
FIG. 9 is a flowchart for describing reproducing processing.

Incidentally, as for the reproducing processing in the flowchart of FIG. 9, description has been made for the processing for performing reproducing in real time with respect to change of the time code; however, in the processing described above, the reproducing apparatus 22 may extract only the image at a timing for displaying the image on the display apparatus 23, edit the image in advance, and reproduce the edited results collectively.

<Example of Execution by Software>

By the way, a series of the processing described above can be executed by hardware; however, it can also be executed by software. When the series of the processing is executed by the software, a program configuring the software is installed from a recording medium to a computer incorporated in dedicated hardware, or, for example, a general purpose personal computer capable of executing various functions by installing various programs.

Figure 11:
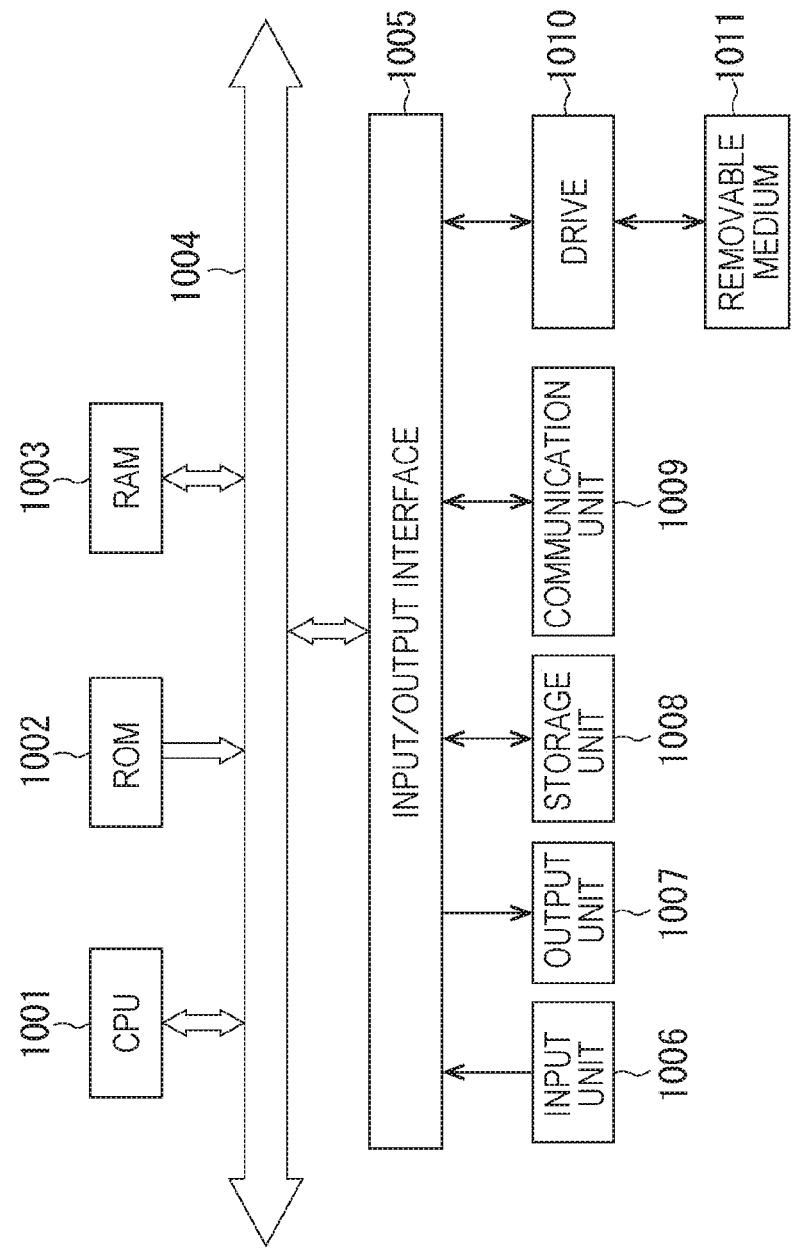
FIG. 11 is a diagram for describing a configuration example of a general purpose personal computer.

FIG. 11 illustrates a configuration example of the general purpose personal computer. The personal computer incorporates a Central Processing Unit (CPU) 1001. The CPU 1001 is connected to an input/output interface 1005 via a bus 1004. The bus 1004 is connected to Read Only Memory (ROM) 1002 and Random Access Memory (RAM) 1003.

The input/output interface 1005 is connected to an input unit 1006 including input devices such as a keyboard, a mouse for a user to input an operation command, an output unit 1007 for outputting to a display device a processing operation screen and an image of a processing result, a storage unit 1008 including a hard disk drive and the like for storing programs and various data, and a communication unit 1009 including a Local Area Network (LAN) adapter and the like for executing communication processing via a network typified by the Internet. In addition, a drive 1010 is connected for reading data from and writing data to a removable medium 1011 such as a magnetic disk (including flexible disk), an optical disk (including Compact Disc-Read Only Memory (CD-ROM), a Digital Versatile Disc (DVD)), a magneto optical disk (including Mini Disc (MD)), or a semiconductor memory.

The CPU 1001 executes various types of processing in accordance with a program stored in the ROM 1002, or a program read from the removable medium 1011, such as the magnetic disk, the optical disk, the magneto optical disk, or the semiconductor memory, to be installed to the storage unit 1008, and loaded to the RAM 1003 from the storage unit 1008. In the RAM 1003, data necessary for the CPU 1001 to execute the various types of processing is also stored appropriately.

In the computer configured as described above, for example, the CPU 1001 loads the program stored in the storage unit 1008 to the RAM 1003 via the input/output interface 1005 and the bus 1004 to execute the series of processing described above.

The program executed by the computer (CPU 1001) can be provided, for example, by being recorded in the removable medium 1011 as a package medium or the like. In addition, the program can be provided via a wired or wireless transmission medium such as a local area network, the Internet, digital satellite broadcasting.

In the computer, the program can be installed to the storage unit 1008 via the input/output interface 1005 by mounting the removable medium 1011 to the drive 1010. In addition, the program can be installed to the storage unit 1008 by receiving with the communication unit 1009 via the wired or wireless transmission medium. Further, the program can be installed in advance to the ROM 1002 and the storage unit 1008.

Incidentally, the program executed by the computer can be a program by which the processing is performed in time series along the order described herein, and can be a program by which the processing is performed in parallel or at necessary timing such as when a call is performed.

In addition, herein, a system means an aggregation of a plurality of constituents (apparatus, module (component), and the like), and it does not matter whether or not all of the constituents are in the same cabinet. Therefore, a plurality of apparatuses that is accommodated in a separate cabinet and connected to each other via a network and one apparatus that accommodates a plurality of modules in one cabinet are both systems.

Incidentally, the embodiment of the present technology is not limited to the embodiments described above, and various modifications are possible without departing from the scope of the present technology.

For example, the present technology can adopt a configuration of cloud computing that shares one function in a plurality of apparatuses via a network to process in cooperation.

In addition, each step described in the above flowchart can be executed by sharing in a plurality of apparatuses, other than being executed by one apparatus.

Further, when a plurality of pieces of processing is included in one step, the plurality of pieces of processing included in the one step can be executed by sharing in a plurality of apparatuses, other than being executed by one apparatus.

Incidentally, the present technology can also adopt the following configuration.

(1) An endoscope apparatus including:
a recording unit for recording an image captured by an image capture unit of an endoscope scope having the image capture unit for capturing an image at a tip of an insertion portion to be inserted into a body cavity;
an assist display control unit for generating as an assist image an image synthesized from information indicating an angle of view of any selected image selected from images recorded in the recording unit and information indicating an angle of view of a captured image that is an image currently captured by the image capture unit; and a display unit for displaying the assist image.

(2) The endoscope apparatus according to (1), wherein the information indicating the angle of view of each of the selected image and the captured image is a mark indicating positions of a center and corners of a corresponding one of the selected image and the captured image.

(3) The endoscope apparatus according to (1), wherein the information indicating the angle of view of each of the selected image and the captured image is an image obtained by edge extraction from a corresponding one of the selected image and the captured image.

(4) The endoscope apparatus according to any one of (1) to (3), further including:
a feature value detection unit for detecting a feature value of the captured image; and
a matching unit for detecting an amount of deviation by matching based on a feature value difference between the captured image and the selected image, wherein the assist display control unit displays information indicating that the assist image cannot be displayed on the display unit when the amount of deviation is greater than a predetermined value.

(5) The endoscope apparatus according to (4), wherein
the matching unit detects a forceps in the captured image and selected image, and
the assist display control unit hides the forceps detected by the matching unit and generates the assist image.

(6) The endoscope apparatus according to any one of (1) to (5), further including:
a feature value detection unit for detecting a feature value of the captured image; and
a recording control unit for recording the captured image in the recording unit in accordance with change of the feature value, wherein
the recording control unit adds an index to the captured image and records the image in the recording unit when a feature value difference that is a difference of a feature value between consecutive images in time series of the captured image is greater than a predetermined value.

(7) The endoscope apparatus according to any one of (1) to (6), wherein
the feature value, when the image is divided into a plurality of blocks, includes a sum of absolute differences between adjacent pixels and a sum total of luminance values in each of the blocks, and a sum of absolute differences between adjacent pixels and a sum total of luminance values of a central block of the blocks.

(8) The endoscope apparatus according to (6) or (7), wherein
the assist display control unit displays a list of images each to which the index is added, of images stored in the recording unit when display of the assist image is requested.

(9) The endoscope apparatus according to (8) wherein
the assist display control unit sets an image selected from the list of the images each to which the index is added, as the selected image.

(10) The endoscope apparatus according to any one of (6) to (9), wherein
the recording control unit deletes an image in order from the oldest to the newest of images recorded in the recording unit, and records the captured image in the recording unit, when a remaining capacity of a storage capacity of the recording unit is less than a predetermined value.

(11) The endoscope apparatus according to any one of (6) to (10), wherein
the recording control unit records a feature value of the captured image and information indicating whether or not display of the assist image is requested, in association with a time code, in addition to the captured image, when recording the captured image in the recording unit.

(12) The endoscope apparatus according to (11), further including
a reproducing unit for reproducing an image of the images recorded in the recording unit correspondingly to the time code, wherein the image is an image at a timing at which display of the assist image is not requested and the feature value difference between images at consecutive different timings is less than a predetermined value.

(13) A method for operating an endoscope apparatus including:
recording an image captured by an image capture unit of an endoscope scope having the image capture unit for capturing an image at a tip of an insertion portion to be inserted into a body cavity;
generating as an assist image an image synthesized from information indicating an angle of view of any selected image selected from images recorded in the recording unit and information indicating an angle of view of a captured image that is an image currently captured by the image capture unit; and
displaying the assist image.

(14) A program for causing a computer to function as:
a recording unit for recording an image captured by an image capture unit of an endoscope apparatus having the image capture unit for capturing an image at a tip of an insertion portion to be inserted into a body cavity;
an assist display control unit for generating as an assist image an image synthesized from information indicating an angle of view of any selected image selected from images recorded in the recording unit and information indicating an angle of view of a captured image that is an image currently captured by the image capture unit; and
a display unit for displaying the assist image.

REFERENCE SIGNS LIST

11 Endoscope scope
21 Endoscope apparatus
22 Reproducing apparatus
23 Display apparatus
31 CCU
32 Display unit
33 Operation unit
51 Camera signal processing unit
52 Feature value detection unit
53 Image recording control unit
54 Recording unit
55 Matching processing unit
56 Assist display control unit
71 Header unit
71a Image capture device
72 Hard mirror (lens barrel)
72a lens barrel axis
73 Light source apparatus

The invention claimed is:
1. An endoscope apparatus, comprising:
an endoscope with an imaging device, wherein a tip of the endoscope is inserted into a body cavity; and
circuitry configured to:
control the imaging device to capture a plurality of images;
record the plurality of images captured by the imaging device;
select a first image from the recorded plurality of images;
record first information indicating a first angle of view of the first image in association with a first time code;
control the imaging device to capture a second image;
record second information indicating a second angle of view of the captured second image in association with a second time code, wherein
the second angle of view is different from the first angle of view,
the first time code corresponds to first insertion of the endoscope, and
the second time code corresponds to a second insertion of the endoscope subsequent to the first insertion;
generate an assist image based on the first information indicating the first angle of view of the first image, the second information indicating the second angle of view of the second image, and third information indicating whether display of the assist image is requested; and control a display device to display the assist image.

2. The endoscope apparatus according to claim 1, wherein the first information includes a mark indicating a position of a center of the first image and positions of corners of the first image, and the second information includes a mark indicating a position of a center of the second image and positions of corners of the second image.

3. The endoscope apparatus according to claim 1, wherein the circuitry is further configured to execute an edge extraction process of each of the first image and the captured second image, to obtain the first information and the second information, respectively.

4. The endoscope apparatus according to claim 1, wherein the circuitry is further configured to:

detect a first feature value of the captured second image;

detect an amount of deviation between the first feature value of the captured second image and a second feature value of the first image, based on a difference between the first feature value and the second feature value; and control an assist display device to display information indicating that the assist image cannot be displayed on the display device based on the amount of deviation that is greater than a threshold value.

5. The endoscope apparatus according to claim 4, wherein the circuitry is further configured to:

detect a forceps in the captured second image and the first image;

hide the detected forceps from each of the first image and the second image; and generate the assist image based on the hidden forceps from each of the first image and the second image.

6. The endoscope apparatus according to claim 1, wherein the circuitry is further configured to:

detect a first feature value of the first image;

record the first image based on a change of the detected first feature value; and add an index to the first image, wherein the first image is recorded based on a feature value difference that is greater than a first threshold value, the feature value difference is a difference between the first feature value of the first image at a first time and a feature value corresponding to a third image at a second time, the first time and the second time are consecutive different timings, and the third image immediately precedes the first image among the plurality of images.

7. The endoscope apparatus according to claim 6, wherein the first feature value, based on a division of the first image into a plurality of blocks, includes:

a sum of absolute differences between adjacent pixels and a sum total of luminance values in each block of the plurality of blocks, and a sum of absolute differences between adjacent pixels and a sum total of luminance values of a central block of the plurality of blocks.

8. The endoscope apparatus according to claim 6, wherein the circuitry is further configured to:

display a list of the plurality of images, add an index to each of the plurality of images based on the request to display the assist image.

9. The endoscope apparatus according to claim 8, wherein the circuitry is further configured to select the first image from the displayed list of the plurality of images.

10. The endoscope apparatus according to claim 6, wherein the circuitry is further configured to:

delete an image in an order from an oldest to a newest of the plurality of images; and record the captured second image based on a capacity of a storage device that is less than a threshold value.

11. The endoscope apparatus according to claim 6, wherein the circuitry is further configured to record the first feature value of the first image.

12. The endoscope apparatus according to claim 11, wherein the circuitry is further configured to:

reproduce an image of the recorded plurality of images associated with the first time code, the image is at a timing at which display of the assist image is not requested and the feature value difference is less than a second threshold value.

13. A method, comprising:

controlling an endoscope with an imaging device to capture a plurality of images, wherein a tip of the endoscope is inserted into a body cavity;

recording the plurality of images captured by the imaging device;

selecting a first image from the recorded plurality of images;

recording first information indicating a first angle of view of the first image in association with a first time code;

controlling the imaging device to capture a second image;

recording second information indicating a second angle of view of the captured second image in association with a second time code, wherein the second angle of view is different from the first angle of view, the first time code corresponds to first insertion of the endoscope, and the second time code corresponds to a second insertion of the endoscope subsequent to the first insertion;

generating an assist image based on the first information indicating the first angle of view of the first image, second information indicating the second angle of view of the second image, and third information indicating whether display of the assist image is requested; and controlling a display device to display the assist image.

14. A non-transitory computer-readable medium having stored thereon computer-executable instructions which when executed by an endoscope apparatus, cause the endoscope apparatus to execute operations, the operations comprising:

controlling an endoscope with an imaging device to capture a plurality of images, wherein a tip of the endoscope is inserted into a body cavity;

recording the plurality of images captured by the imaging device;

selecting a first image from the recorded plurality of images;

recording first information indicating a first angle of view of the first image in association with a first time code;

controlling the imaging device to capture a second image;

recording second information indicating a second angle of view of the captured second image in association with a second time code, wherein the second angle of view is different from the first angle of view, the first time code corresponds to first insertion of the endoscope, and the second time code corresponds to a second insertion of the endoscope subsequent to the first insertion;

generating an assist image based on the first information indicating the first angle of view of the first image, second information indicating the second angle of view of the second image, and third information indicating whether display of the assist image is requested; and controlling a display device for displaying the assist image.

15. An endoscope apparatus, comprising:

an endoscope with an imaging device, wherein a tip of the endoscope is inserted into a body cavity; and circuitry configured to:
 control the imaging device to capture a plurality of images;
 record each of the plurality of images captured by the imaging device;
 select a first image from the plurality of images;
 record first information indicating an angle of view of the first image in association with a time code;
 control the imaging device to capture a second image, wherein the second image is different from the plurality of images;
 generate an assist image based on the first information indicating the angle of view of the first image, second information indicating an angle of view of the captured second image, and third information indicating whether display of the assist image is requested;
 control a display device to display the assist image;
 detect a first feature value of the first image;
 record the first image based on a change of the detected first feature value;
 add an index to the first image, wherein
  the first image is recorded when a feature value difference is greater than a first threshold value,
  the feature value difference is a difference between the first feature value of the first image at a first time and a feature value corresponding to a third image at a second time,
  the first time and the second time are consecutive different timings, and
  the third image immediately precedes the first image among the plurality of images;
 record, when the first image is recorded, the first feature value of the first image; and
 reproduce an image of the plurality of images associated with the time code, wherein
  the image is at a timing at which display of the assist image is not requested and the feature value difference is less than a second threshold value.

* * * * *